(12) United States Patent
Mohammadi et al.

(10) Patent No.: US 6,503,517 B1
(45) Date of Patent: Jan. 7, 2003

(54) COSMETIC COMPOSITIONS WITH MENTHOL

(75) Inventors: Fatemeh Mohammadi, Hebron, CT (US); Anthony Vargas, Monroe, CT (US)

(73) Assignee: Conopco, Inc., New York, NY (US)

( * ) Notice: Subject to any disclaimer, the term of this patent is extended or adjusted under 35 U.S.C. 154(b) by 0 days.

(21) Appl. No.: 09/544,027

(22) Filed: Apr. 6, 2000

Related U.S. Application Data

(60) Provisional application No. 60/178,992, filed on Jan. 28, 2000.

(51) Int. Cl.⁷ .................................................. A61K 7/00
(52) U.S. Cl. ........................................ 424/401; 424/747
(58) Field of Search ................................... 424/401, 474

(56) References Cited

U.S. PATENT DOCUMENTS

| | | | |
|---|---|---|---|
| 5,753,210 A | * 5/1998 | McEleney et al. | 424/59 |
| 5,833,973 A | 11/1998 | Dobkowski et al. | 424/18.08 |
| 5,833,998 A | * 11/1998 | Biedermann et al. | 424/401 |
| 5,853,741 A | 12/1998 | Znaiden et al. | 424/401 |
| 5,854,336 A | 12/1998 | Divone, Sr. et al. | 524/588 |
| 6,183,766 B1 | * 6/2001 | Sine et al. | 424/405 |

OTHER PUBLICATIONS

John A. Wenninger and G.N. McEwen, Jr., Ph.D., J.D., International Cosmetic Ingredient Dictionary and Handbook, 1997, THer Cosmetic, Toiletry, and Fragnance Association, Seventh Edition, vol. 1, pp. 810–811.*

* cited by examiner

*Primary Examiner*—Michael G. Hartley
*Assistant Examiner*—Konata M. George
(74) *Attorney, Agent, or Firm*—Milton L. Honig

(57) ABSTRACT

A cosmetic composition is provided which includes menthol suspended in a carrier system of a crosslinked non-emulsifying siloxane elastomer and a volatile siloxane. The carrier system prevents crystallization and granulation of menthol from the cosmetic compositions.

4 Claims, No Drawings

COSMETIC COMPOSITIONS WITH MENTHOL

This application claims priority from Provisional Application Serial No. 60/178,992 filed Jan. 28, 2000.

BACKGROUND OF THE INVENTION

1. Field of the Invention

The invention concerns cosmetic compositions formulated with menthol and its derivatives.

2. The Related Art

Somatic sensation enables our bodies to feel, ache and react to temperature changes. The reactions occur when skin sensory receptors throughout the body are stimulated by mechanical, physical or chemical contact. Different receptors are responsible for different stimuli; these are categorized as pain, pressure or temperature changes. Special pathways exist for face sensations. The trigeminal nerve is located on the right side of the face. It extends beyond the ear, underneath and branches out towards the cheek area. Properly formulated cosmetic compositions can stimulate the receptors to produce very positive pleasant effects.

One of the oldest stimulants is 1-menthol; it imparts a cooling sensation to the skin. Menthol and related terpenes do not really cool through the effect of latent cold. Actually they heighten the perception of cold in the nerve endings in the skin, so that the surface of skin "feels cold".

A problem with menthol is dissolving or uniformly dispersing the compound in a cosmetic delivery system. After storage, in many systems menthol has a tendency to crystallize. Severe crystallization leads to granulation effects being perceived by a consumer. Granulation is particularly evident in anhydrous systems.

Accordingly, it is an object of the present invention to provide a cosmetic composition formulated with menthol which avoids crystallization and the aesthetically displeasing effects of granulation.

Another object of the present invention is to provide a cosmetic composition incorporating menthol which enhances pleasant skin sensations while minimizing any negative properties of menthol.

These and other objects of the present invention will become more readily apparent from consideration of the following summary and detailed description.

SUMMARY OF THE INVENTION

A cosmetic composition is provided which includes:

(i) from about 0.1 to about 30% of a crosslinked non-emulsifying siloxane elastomer;

(ii) from about 1 to about 80% of a volatile polyorganosiloxane; and (iii) from about 0.0001 to about 5% of menthol.

DETAILED DESCRIPTION OF THE INVENTION

Now it has been found that menthol can be suspended without fear of crystallization in a vehicle delivery system of a crosslinked non-emulsifying siloxane elastomer and a volatile polyorganosiloxane. Moreover, the effectiveness of menthol in providing a cooling sensation to the skin is enhanced when delivered in the elastomer and volatile polyorganosiloxane vehicle.

Crosslinked non-emulsifying siloxane elastomers are a first essential element of this invention. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl compound, particularly a polymer with at least two free vinyl groups, reacting with Si—H linkages of a polysiloxane backbone such as a molecularly spherical MQ resin. Elastomer compositions are commercially available from the General Electric Company under product designation General Electric Silicone 839 with CTFA name of Cyclomethicone and Vinyl Dimethicone/Methicone Cross Polymer, delivered as 5–7.5% elastomer in a cyclomethicone carrier, and under the designation Polysilicone-11. A related elastomer composition under the CTFA name of Crosslinked Stearyl Methyl Dimethyl Siloxane Copolymer is available as Gransil SR-CYC (25–35% elastomer in cyclomethicone) from Grant Industries, Inc., Elmwood Park, N.J. The commercial products from General Electric and Grant Industries may be further processed by subjecting them to a high pressure (approximately 5,000 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is best when ranging between 300 and 20,000 cps at 25° C. as measured by a Brookfield LV Viscometer (size 4 bar. 60 rpm. 15 sec.).

Amounts of the elastomer may range from about 0.1 to about 30%, preferably from about 1 to about 15%, optimally from about 3 to about 10% by weight.

A second element of the present invention is that of a volatile polyorganosiloxane. The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxane containing from about 3 to about 9 silicone atoms. The linear volatile silicones generally have viscosities of less then about 5 centistokes at 25° C., while the cyclic materials have viscosities of less than about 10 centistokes, the preferable range being from 0.1 to 8 centistokes. Examples of volatile silicone oils useful in the present invention include: Dow Corning 224, Dow Corning 245, Dow Corning 344, Dow Corning 345 and Dow Corning 200 (manufactured by the Dow Corning Corporation); Silicone 7207 and Silicone 7158 (manufactured by the Union Carbide Corporation); and SF1202 (manufactured by General Electric).

Amounts of the volatile polyorganosiloxane will range from about 1 to about 80%, preferably from about 20 to about 70%, optimally from about 30 to about 65% by weight.

Menthol is another essential element of the present invention. The material may be in dextro, levo or racemic form although the levo form is preferred. Amounts may range from about 0.0001 to about 5%, preferably from about 0.01 to about 2%, more preferably from about 0.1 to about 1%, optimally from about 0.2 to about 0.5% by weight of the cosmetic composition.

Cosmetic compositions of the present invention are particularly preferred when in the anhydrous form (less than about 5% water, preferably less than about 1% water). Yet oil and water emulsions may also be suitable for the present invention. Whether anhydrous or emulsion type, compositions of the present invention may further include a variety of pharmaceutically acceptable carriers and skin actives. Amounts of the carrier may range from about 1 to about 95%, preferably from about 5 to about 70%, optimally from about 10 to about 40% by weight. Among the carriers are emollients, water, inorganic powders, foaming agents, surfactants and combinations thereof.

Emollients are substances selected from polyols, esters and hydrocarbons. Polyols suitable for the invention may include propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin, xylitol and mixtures thereof.

Esters useful as emollients include:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate and oleyl oleate.

(3) Ether-esters such as fatty acid esters of ethoxylated fatty alcohols.

(4) Polyhydric alcohol esters. Ethylene glycol mono- and di-fatty acid esters, diethylene glycol mono- and di-fatty acid esters, polyethylene glycol (200–6000) mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterol esters, of which cholesterol fatty acid esters are examples thereof.

Illustrative hydrocarbons are mineral oil, polyalphaolefins, petrolatum, isoparaffin, polybutenes and mixtures thereof.

Inorganic powders are useful carriers. Examples include clays (such as Montmorillonite, Hectorite, Laponite and Bentonite), talc, mica, silica, alumina, zeolites, sodium sulfate, sodium bicarbonate, sodium carbonate, calcium sulfate and mixtures thereof.

Aerosol propellants may also be used as carriers. Propellants are normally based on volatile hydrocarbons such as propane, butane, isobutane, pentane, isopropane and mixtures thereof. Phillips Petroleum Company is a source of such propellants under trademarks including A31, A32, A51 and A70. Halocarbons including fluorocarbons and dimethyl ether are further widely employed propellants.

Surfactants may constitute at least a portion of the carrier for compositions according to the present invention. These may be selected from nonionic, anionic, cationic or amphoteric emulsifying agents. They may range in amount anywhere from about 0.1 to about 20% by weight. Illustrative nonionic surfactants are alkoxylated compounds based on $C_{10}$–$C_{22}$ fatty alcohols and acids and sorbitan. These materials are available, for instance, from the Shell Chemical Company under the Neodol trademark. Copolymers of polyoxypropylenepolyoxyethylene sold by the BASF Corporation under the Pluronic trademark are sometimes also useful. Alkyl polyglycosides available from the Henkel Corporation may also be utilized for purposes of this invention.

Anionic type surfactants include fatty acid soaps, sodium lauryl sulphate, sodium lauryl ether sulphate, alkyl benzene sulphonate, mono- and di-alkyl acid phosphates, sarcosinates, taurates and sodium fatty acyl isethionate.

Amphoteric surfactants include such materials as dialkylamine oxide and various types of betaines (such as cocamidopropyl betaine).

Among the skin actives may be included Vitamin C and its derivatives, alpha- and beta-hydroxycarboxylic acids, retinoids, sunscreens, botanical extracts and sunless tanners. Vitamin C covers ascorbic acid, magnesium ascorbate, ascorbyl tetra fatty esters such as the tetraisopalmitate and similar derivatives. Suitable alpha-hydroxycarboxylic acids include glycolic, lactic, malic and hydroxycaprylic acids. Salicylic acid is representative of the beta-hydroxycarboxylic acids. By the term "acids" is meant to include salts such as alkali metal and ammonium salts thereof. Examples of retinoids include retinol, retinoic acid, retinyl palmitate, retinyl linoleate and retinyl acetate. Botanical extracts include aloe, chamomile, borage, green tea, sage, yarrow, genistein, tulsi, kamala, rosemary, henna, lavender, sandalwood, eucalyptus and combinations thereof. Sunless tanners are particularly represented by dihydroxyacetone and sugars (e.g. xylitol). Sunscreens are those materials having at least one chromophoric group absorbing within the ultraviolet range somewhere from 290 to 400 nm. Particularly useful sunscreens are benzophenone-3, octyl dimethyl PABA, butyl methoxy dibenzoylmethane, octyl methoxycinnamate and octocrylene.

Amounts of the skin actives will depend upon the particular substance. Generally they may range from about 0.0001 to about 30%, preferably from about 0.01 to about 20%, more preferably from about 0.1 to about 10%, optimally from about 0.5 to about 5% by weight of the cosmetic composition.

Minor adjunct ingredients may also be included in cosmetic compositions of this invention. These ingredients may be selected from preservatives, fragrances, anti-foam agents, opacifiers, colorants and mixtures thereof, each in their effective amounts to accomplish their respective functions.

The compositions of the present invention may be applied to a variety of cosmetics. Most particularly they are suitable for skin creams and lotions. However, the compositions will have applicability to hair care products such as shampoos, conditioners, styling gels and hair sprays; shaving products (shaving foam, aftershave lotion); underarm products (antiperspirants and deodorants); personal wash products (toilet bars and body wash liquids); perfume and cologne; and lip care products (lipstick and lip balm), all of which are merely illustrative.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

A typical Vitamin C skin cream formulation is reported in Table I.

TABLE I

| COMPONENT | WEIGHT % |
|---|---|
| Cyclomethicone | 36.0 |
| Crosslinked Silicone Elastomer In Cyclomethicone (25% Active) | 24.0 |
| Propylene Glycol | 20.5 |
| Polyethylene Glycol 200 | 10.5 |
| Dimethyl Isosorbide | 2.0 |
| Ascorbic Acid | 5.0 |
| Menthol | 1.2 |
| Cetyl Dimethicone Copolyol | 0.8 |

EXAMPLE 2

A foaming skin cosmetic formulation is illustrated in Table II. The formulation is intended for delivery via a non-aerosol mechanical pump.

TABLE II

| COMPONENT | WEIGHT % |
|---|---|
| PHASE A | |
| Carbopol 1382 ® (2% Active) | 5.0 |
| Disodium EDTA | 0.1 |
| Butylene Glycol | 1.7 |
| Glycerin | 1.9 |
| Allantoin | 0.2 |
| Colorant | 0.12 |
| Water | Bal. |
| PHASE B | |
| Primrose Oil | 1.0 |
| Elefac-205 ® | 3.0 |
| Borage Oil | 1.0 |
| Tridecylsalicylate | 2.0 |
| Alpha-Bisabolol | 0.1 |
| Glyceryl Stearate | 1.0 |
| Cetyl Alcohol | 1.5 |
| Vitamin E Acetate | 0.5 |
| Preservatives | 0.4 |
| Amphisol A ® | 2.0 |
| PHASE C | |
| Water | 1.8 |
| Triethanolamine | 1.0 |
| Panthenol | 0.2 |
| PHASE D | |
| Cyclomethicone | 2.0 |
| Silicone Elastomer (7.5% Elastomer Solids in Cyclomethicone) | 25.0 |
| Menthol | 1.0 |
| Fragrance | 0.2 |

EXAMPLE 3

A typical sunscreen formulation according to the present invention is reported in Table III.

TABLE III

| INGREDIENT | WEIGHT % |
|---|---|
| Phase A | |
| Deionized Water | balance |
| Disodium EDTA | 0.10 |
| Glycerin | 1.50 |
| Sodium Chloride | 3.00 |
| Butylene Glycol | 2.50 |
| Phase B | |
| Octymethoxycinnamate | 7.50 |
| Octyl Salicylate | 5.00 |
| Phenonip | 0.60 |
| Vitamin E Acetate | 0.50 |
| Retinyl Linoleate | 0.01 |
| Aluminum Stearate | 5.00 |
| Dow Corning 5225C (Cyclomethicone/Dimethicone Copolyol) | 10.00 |
| Cetyl Dimethicone | 1.00 |
| DC 345 (Cyclomethicone) | 2.00 |
| Crosslinked Silicone Elastomer in Cyclomethicone (25% Active) | 30.00 |
| ABIL-EM 97 ® | 1.00 |
| Menthol | 1.00 |
| Fragrance | 0.15 |

EXAMPLE 4

A lipstick formulation according to the present invention is reported in Table IV.

TABLE IV

| INGREDIENT | WEIGHT % |
|---|---|
| PHASE A | |
| Castor Oil | 16.33 |
| Ozokerite | 3.10 |
| Carnauba | 1.00 |
| Candelillate | 4.20 |
| Beeswax | 3.36 |
| Lanolin Ultra | 5.00 |
| Softisan 649 ® (Triglyceride Wax) | 4.00 |
| Butylated Hydroxytoluene | 0.18 |
| Hydroxylated Lanolin | 0.50 |
| Mango Butter | 2.00 |
| Tridecyl Salicylate | 0.50 |
| Rice Bran Oil | 3.00 |
| Parsol MCX ® | 7.00 |
| Benzophenone 3 | 4.00 |
| Tocopherol | 1.50 |
| Sunflower Monoglycerides | 3.50 |
| Lecithin | 1.00 |
| Phase B | |
| Oryzanol | 0.25 |
| Rice Starch | 3.00 |
| Phase C | |
| Red #6 | 2.40 |
| Titanium Dioxide | 0.40 |
| Blue #1 | — |
| Yellow Iron Oxide | 1.63 |
| PHASE D | |
| Timica Silkwhite | 4.40 |

TABLE IV-continued

| INGREDIENT | WEIGHT % |
| --- | --- |
| PHASE E | |
| Water | Balance |
| Trehalose | 1.00 |
| Green Tea | 1.00 |
| Ginko Biloba | 0.50 |
| Aloe Vera Powder | 0.10 |
| Neosorb ® (Sorbitol) | 2.00 |
| PHASE F | |
| Crosslinked Silicone Elastomer in Cyclomethicone (25% Active) | 13.71 |
| Menthol | 1.00 |
| Anethole | 0.01 |
| PHASE G | |
| Fragrance/Flavor | 0.70 |

EXAMPLE 5

An after sun lotion according to the present invention is reported in Table V.

TABLE V

| INGREDIENT | WEIGHT % |
| --- | --- |
| PHASE A | |
| Deionized Water | 29.13 |
| Aloe Powder | 0.50 |
| Carbopol 1382 ® (2% Active) | 10.00 |
| Butylene Glycol | 4.21 |
| Glycerin | 0.20 |
| Allantoin | 0.50 |
| Trehalose | 0.50 |
| PHASE B | |
| Squalane | 5.00 |
| Cetyl Alcohol | 1.00 |
| Beeswax | 6.80 |
| Petrolatum Jelly | 4.00 |
| Lanolin | 2.00 |
| BRIJ 76 | 2.25 |
| Glyceryl Stearate | 1.75 |
| Cetyl Phosphate | 0.25 |
| Polydecene | 8.00 |
| Phenonip ® | 0.58 |
| PHASE C | |
| Vitamin E Acetate | 0.50 |
| Cyclomethicone | 1.00 |
| Dimethicone Copolyol | 1.00 |
| Retinyl Linoleate | 0.10 |
| Menthol | 2.00 |
| Crosslinked Silicone Elastomer in Cyclomethicone (7.5% Solid Elastomer) | 10.00 |
| DL-Panthanol | 0.20 |
| Triethanolamine | 0.70 |
| Deionized Water | 6.33 |
| Botanical Extract | 1.00 |

EXAMPLE 16

A lip balm formulation according to the present invention is illustrated in Table VI.

TABLE VI

| INGREDIENT | WEIGHT % |
| --- | --- |
| PHASE A | |
| Babassuu Oil | 37.40 |
| Pentaerythrityl Tetraisostearate | 25.00 |
| Lanolin Wax | 4.00 |
| Beeswax | 7.00 |
| Petrolatum | 5.00 |
| Glyceryl Behenate | 3.00 |
| Microcrystalline Wax | 4.00 |
| Propyl Paraben | 0.10 |
| PHASE B | |
| Cyclomethicone | 1.00 |
| Vitamin E Acetate | 0.50 |
| Crosslinked Silicone Elastomer in Cyclomethicone (7.5% Solid Elastomer) | 10.00 |
| Dimethicone Copolyol | 1.00 |
| Menthol | 2.00 |

EXAMPLE 7

A depilatory formulation according to the present invention is described in Table VII.

TABLE VII

| INGREDIENT | WEIGHT % |
| --- | --- |
| PHASE A | |
| Deionized Water | 53.90 |
| Xanthan Gum (2% Solution) | 10.00 |
| Disodium EDTA | 0.10 |
| Butylene Glycol | 1.00 |
| Urea | 4.00 |
| Allantoin | 0.20 |
| PHASE B | |
| Decyl Oleate | 3.00 |
| Bean Tree Oil | 2.00 |
| Ceteareth-12 | 2.00 |
| Cetearyl Alcohol | 2.00 |
| Phenonip ® | 0.45 |
| PHASE C | |
| Crosslinked Silicone Elastomer in Cyclomethicone (7.5% Solid Elastomer) | 10.00 |
| Cyclomethicone | 1.00 |
| Menthol | 1.00 |
| Fragrance | 0.30 |

EXAMPLE 8

An aerosol shaving foam according to the present invention is described in Table VIII.

TABLE VIII

| INGREDIENT | WEIGHT % |
| --- | --- |
| PHASE A | |
| Deionized Water | 71.25 |
| Sorbitol (70%) | 5.00 |
| Sodium Hydroxide (10% Solution) | 2.00 |
| PHASE B | |
| Myristic Acid | 3.00 |
| Bean Tree Oil | 1.00 |
| Stearic Acid | 4.00 |
| Penonip ® | 0.45 |

TABLE VIII-continued

| INGREDIENT | WEIGHT % |
| --- | --- |
| PHASE C | |
| Dimethicone Copolyol | 1.00 |
| Crosslinked Silicone Elastomer in Cyclomethicone (7.5% Solid Elastomer) | 10.00 |
| Cyclomethicone | 1.00 |
| Menthol | 1.00 |
| Fragrance | 0.30 |

EXAMPLE 9

An after shave lotion according to the present invention is reported in Table IX.

TABLE IX

| INGREDIENT | WEIGHT % |
| --- | --- |
| PHASE A | |
| Deionized Water | 38.23 |
| Carbopol 1382 ® (2% Solution) | 5.00 |
| Xanthan Gum (2% Solution) | 10.00 |
| Disodium EDTA | 0.10 |
| Butylene Glycol | 1.00 |
| Allantoin | 0.20 |
| PHASE B | |
| Isostearyl Isostearate | 3.00 |
| Bean Tree Oil | 2.00 |
| Benzophenone-3 | 2.00 |
| Stearyl Alcohol | 1.20 |
| Steareth-2 | 2.62 |
| Steareth-21 | 0.87 |
| Phenonip ® | 0.45 |
| PHASE C | |
| Crosslinked Silicone Elastomer in Cyclomethicone (7.5% Solid Elastomer) | 10.00 |
| Cyclomethicone | 1.00 |
| Menthol | 1.00 |
| Fragrance | 3.00 |
| PHASE D | |
| Sodium Hydroxide (10% Solution) | 0.50 |
| PHASE E | |
| Deionized Water | 1.83 |
| Ethyl Alcohol | 16.00 |

EXAMPLE 10

A facial foundation according to the present invention is described in Table X.

TABLE X

| INGREDIENT | WEIGHT % |
| --- | --- |
| PHASE A | |
| Dimethicone and Dimethicone Copolyol | 7.00 |
| Bean Tree Oil | 3.00 |
| Vitamin E Acetate | 0.05 |
| Propyl Paraben | 0.10 |
| PHASE B | |
| Cyclomethicone | 1.00 |
| Silicone Powder | 1.50 |
| Pigment | 1.50 |
| Crosslinked Silicone Elastomer in | 15.00 |

TABLE X-continued

| INGREDIENT | WEIGHT % |
| --- | --- |
| Cyclomethicone (7.5% Solid Elastomer) | |
| Dimethicone Copolyol | 1.00 |
| Menthol | 1.00 |
| PHASE C | |
| Deionized Water | 66.80 |
| Disodium EDTA | 0.10 |
| Butylene Glycol | 1.00 |
| Allantoin | 0.20 |
| Methyl Paraben | 0.30 |

EXAMPLE 11

An antiperspirant gel formulation according to the present invention is reported in Table XI.

TABLE XI

| INGREDIENT | WEIGHT % |
| --- | --- |
| PHASE A | |
| Cyclomethicone | 5.00 |
| Crosslinked Silicone Elastomer in Cyclomethicone (7.5% Solid Elastomer) | 10.00 |
| Menthol | 1.00 |
| Dimethicone 200 Fluid (50 cst) | 5.00 |
| Stearyl Heptonoate | 1.00 |
| PHASE B | |
| Bean Tree Oil | 1.00 |
| PPG Butyl Ether | 15.00 |
| Aluminum Zirconium Tetrachlorohydrox Glycinate | 44.70 |
| Hydroxylated Milk Glyceride | 2.00 |
| Fragrance | 0.30 |

EXAMPLE 12

An anhydrous mask was formulated to evaluate the stability enhancing effect of the cross-linked non-emulsifying siloxane and elastomers of the present invention with respect to menthol. Table XII lists a test and a control mask composition. Formulation A combines menthol with the siloxane elastomer while Formulation B is a control containing none of the elastomer. These formulations were subjected to a freeze/thaw cycle of 0° C. and 25° C. in alternate 24 hour periods for a total of six days. The formulations were then evaluated for menthol crystallization using a DermaVision Micrograph System. The system consisted of a Sony Color Video Camera (Model DXC9000) coupled to a Zeiss Microscope (Model SV11) operating with a polarizing attachment (Fostec Inc) to a light source. Camera and microscope were connected to a video camera interfaced with a computer KS200 Software (Carl Zeiss Inc.). Micrographs of Formulation A revealed no crystalli zation of menthol while the micrograph of control Formulation B possessed considerable amounts of crystallized menthol. Storage stability was evidently enhanced by the presence of the cross-linked siloxane elastomer.

TABLE XII

| INGREDIENTS | FORMULATION A (WEIGHT %) | FORMUALTION B (WEIGHT %) |
|---|---|---|
| PHASE A | | |
| Versagel M750 ®* | 50.0 | 50.0 |
| Behenyl Behenate | 5.00 | 5.00 |
| Silicone Powder | 2.00 | 2.00 |
| Salicylic Acid | 1.00 | 1.00 |
| PHASE B | | |
| Crosslinked Silicone Elastomer in Cyclomethicone (7.5% Solid Elastomer) | 30.00 | — |
| Cyclomethicone | — | 30.00 |
| Menthol | 1.00 | 1.00 |
| Tridecyl Salicylate | 10.00 | 10.00 |

*Mineral Oil with Hydrogenated Ethylene/Propylene/Styrene Copolymer

The foregoing description and examples illustrate selected embodiments of the present invention. In light thereof variations and modifications will be suggested to one skilled in the art, all of which are within the spirit and purview of this invention.

What is claimed is:

1. A cosmetic composition comprising:

(i) from about 0.1 to about 30% of a crosslinked non-emulsifying siloxane elastomer;

(ii) from about 1 to about 80% of a volatile polyorganosiloxane; and (iii) from about 0.0001 to about 5% of menthol in levo form, the menthol being suspended without crystallization in the siloxane elastomer and providing an enhanced cooling sensation to skin when delivered in the siloxane elastomer.

2. The composition according to claim 1 wherein the crosslinked non-emulsifying siloxane elastomer is formed from a divinyl monomer reacting with the Si—H linkages of a siloxane backbone.

3. The composition according to claim 1 wherein the volatile siloxane is cyclomethicone.

4. A cosmetic composition comprising:

(i) from about 0.1 to about 30% of a crosslinked non-emutsifying siloxane elastomer;

(ii) from about 1 to about 80% of a volatile polyorganosiloxane; and (iii) from about 0.0001 to about 5% of menthol in the levo form.

* * * * *